(12) United States Patent
Bronkalla

(10) Patent No.: US 10,537,292 B2
(45) Date of Patent: Jan. 21, 2020

(54) AUTOMATED CALIBRATION AND QUALITY ASSURANCE OF MEDICAL IMAGES

(71) Applicant: INTERNATIONAL BUSINESS MACHINES CORPORATION, Armonk, NY (US)

(72) Inventor: Mark Bronkalla, Hartland, WI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 275 days.

(21) Appl. No.: 15/258,859

(22) Filed: Sep. 7, 2016

(65) Prior Publication Data

US 2018/0068466 A1    Mar. 8, 2018

(51) Int. Cl.
*G06T 11/00* (2006.01)
*A61B 6/00* (2006.01)

(52) U.S. Cl.
CPC .............. *A61B 6/00* (2013.01); *A61B 6/585* (2013.01)

(58) Field of Classification Search
CPC ........ A61B 6/037; A61B 6/5235; A61B 6/585; G06T 7/0028; G06T 11/60; G06T 11/005
See application file for complete search history.

(56) References Cited

U.S. PATENT DOCUMENTS

| | | | |
|---|---|---|---|
| RE44,982 E | 7/2014 | Cheong et al. | |
| 2008/0076967 A1* | 3/2008 | Couvillon, Jr. ..... | A61B 1/00059 600/117 |
| 2010/0147961 A1* | 6/2010 | Jancke ............. | G06K 19/06037 235/494 |
| 2014/0049635 A1* | 2/2014 | Laffargue ............ | G01F 25/0084 348/135 |
| 2014/0350395 A1* | 11/2014 | Shachaf ................ | G06T 7/0012 600/431 |
| 2015/0281507 A1 | 10/2015 | Konen et al. | |
| 2016/0081533 A1* | 3/2016 | Couvillon, Jr. ..... | A61B 1/00059 348/65 |

* cited by examiner

*Primary Examiner* — Duy M Dang
(74) *Attorney, Agent, or Firm* — Erik Huestis; Stephen Kenny; Foley Hoag

(57) ABSTRACT

Self-describing calibration targets for inclusion in medical imagery and automated quality control and calibration are provided. In various embodiments, a medical image is received. The medical image includes a calibration target in its field of view. A description of the calibration target is read from the calibration target. The description includes size and at least one color reference. Based on the description of the calibration target, correction parameters are determined for the medical image. The correction parameters include pixel shape correction parameters, scale correction parameters, contrast correction parameters, or color correction parameters.

20 Claims, 4 Drawing Sheets

US 10,537,292 B2

AUTOMATED CALIBRATION AND QUALITY ASSURANCE OF MEDICAL IMAGES

BACKGROUND

Embodiments of the present invention relate to automated calibration of medical imagery, and more specifically, to a self-describing calibration target for inclusion in medical imagery and automated quality control and calibration.

BRIEF SUMMARY

According to embodiments of the present disclosure, methods of and computer program products for automated calibration of medical imagery are provided. A medical image is received. The medical image includes a calibration target in its field of view. A description of the calibration target is read from the calibration target. The description includes size and at least one color reference. Based on the description of the calibration target, correction parameters are determined for the medical image. The correction parameters include pixel shape correction parameters, scale correction parameters, contrast correction parameters, or color correction parameters.

DETAILED DESCRIPTION

Figure 1:
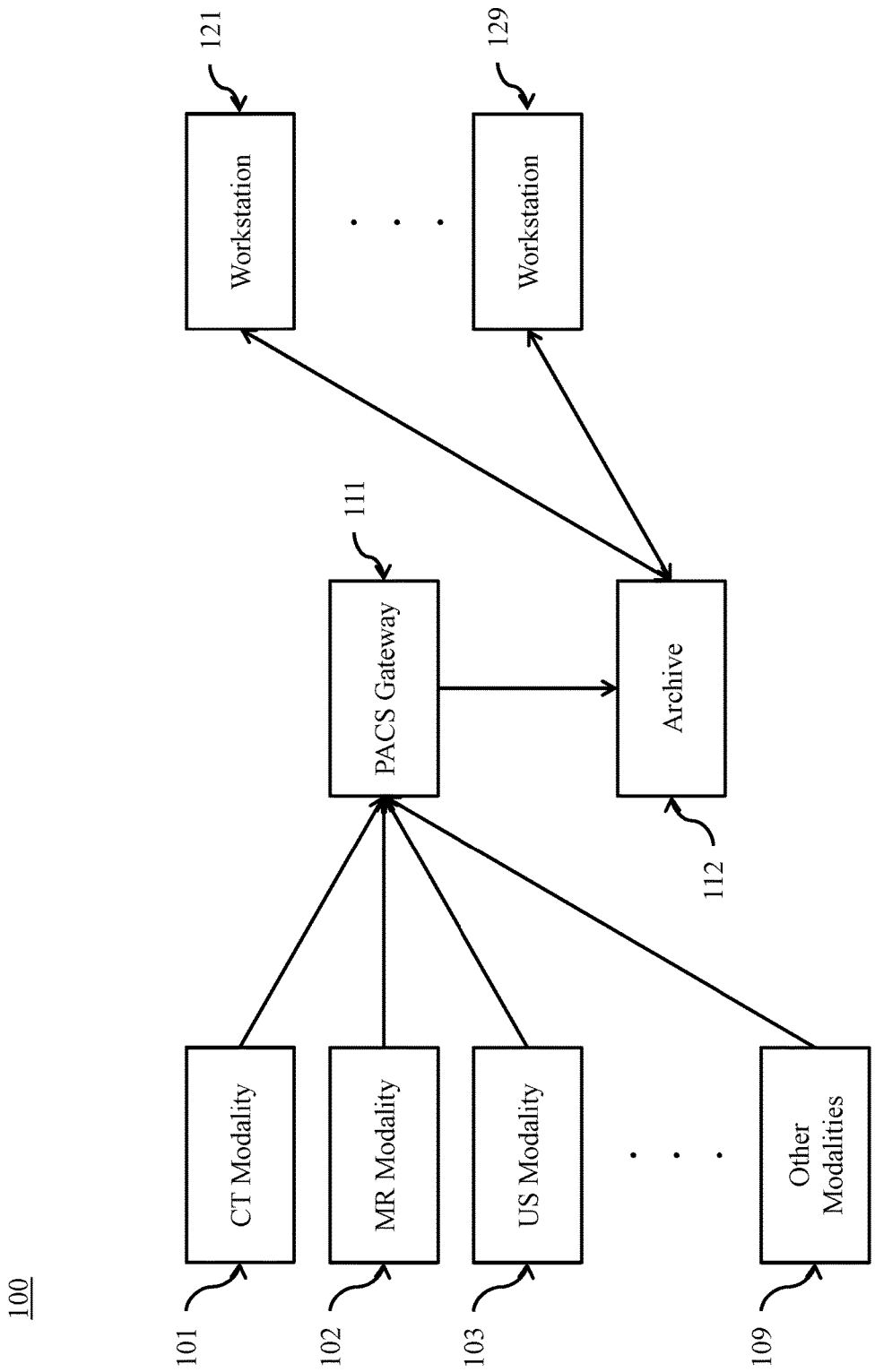
FIG. 1 depicts an exemplary Picture Archiving and Communication System.

A Picture Archiving and Communication System (PACS) is a medical imaging system that provides storage and access to images from multiple modalities. In many heathcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

Photos and movies are becoming increasingly common in medical imaging. Photographic images may be acquired and sent to the PACS for use in diverse fields such as surgery, dermatology, orthopedics and others. However, common problems include lack of pixel size calibration and characterization of the lighting. Pixel size calibration is needed for measurements of the anatomy, whether directly or in a serial comparison against other images of the same anatomy to show changes in size. For example, serial comparison is used to monitor tumor growth, spread of an infection, or spread of inflammation. Lighting is also problematic in that the lighting conditions, such as color temperature, light type (e.g., incandescent, fluorescent, daylight), and the color rendering index are not controlled in many clinical settings. Additionally, the user is often not technically trained in photography and may be using consumer technology such as a smart phone or point and shoot camera.

Color is important, for example, in judging skin color (e.g., checking for jaundice), monitoring the spread of infection or inflammation (e.g., a red ring may have varying detectability in differing lighting conditions), or characterizing a lesion (e.g., judging the color of a possible melanoma). Many images are captured with limited color bit depth, so correction post processing may not be feasible. In addition, in many cases the field of view may be dominated by certain colors that would otherwise throw off automatic white balance, such as skin tones, blue or green sterile drapes, or blood.

To manage these problems, in various embodiments of the present disclosure, a small calibration object is included within the image. In some embodiments, the calibration object is also self-describing to minimize error and aid in automated calibration or correction. Calibration objects according to embodiments of the present disclosure may be present on items that are naturally in the field of view, may be sterile, may be microscopic, and may be subject to patient captured follow-up images.

In some embodiments, a standardized target is provided that may be recognized by image capture software and automatically used for white balance correction. In this way, further automation and color accuracy may be provided. Further, by avoiding user input of the size of the image object, further sources of user error are avoided.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
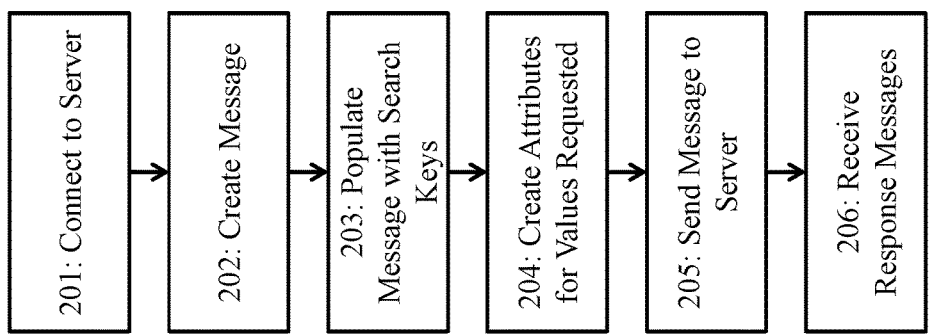
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

The present disclosure provides for the generation of calibration information including size and color for medical images, thereby solving a common problem in enterprise imaging. In particular, proper calibration is a significant problem where simple consumer photography equipment is used for medical images (e.g., dermatology or wound care).

One of the problems that is encountered is that a user may often not take the photograph from a point that is exactly perpendicular to the object or patient. This means that there will be parallax error or foreshortening error if the user calibrates the image in one direction and assumes that it is correct for measurements in any direction. Through the use of a circle or regular polygon for the sizing object, the foreshortening can be detected as differences in the maximum and minimum measured diameters of the calibration object. A correction to the pixel calibration values may then be computed separately for the X and Y dimensions. When using a camera to auto detect the calibration object and apply the calibration values to the image header, the system may alert the user based on configurable rules settings that the parallax error is unacceptably large and that they should re-take the image.

When using a camera to auto detect the calibration object and verify the grey scale calibrations, detecting under or over exposure configurable rules may be used to set the quality threshold. In some embodiments, this includes differentiating 0% and 5% white as well as 95% and 100% white. However, in various embodiments this is configurable to other values, and thus some calibration target include grey swatches.

Whether and how the calibration information is displayed may be governed by preferences related to the user, organization, exam type, imaged organ, or other attributes of the image. For example, a diagram may be superimposed on the image or part of the image to show the end user the parallax or vantage point of the observer. If multiple images are obtained of the same target area, the parallax information may be used to create a composite image, such that a user can view the tissue from multiple vantage points by providing an input via a mouse, joystick, or other such input device.

Certain cameras include while balance, but automatic calibration often assumes that the photographed scene should have an average white balance level. Medical imagery fails with this technique due to common preponderance of certain colors. Calibration objects according to embodiments of the present disclosure provide a known white balance swatch or target that can be automatically recognized. In some embodiments, the swatch is printed on a neutral grey material (e.g., steel) without compromising its function.

In some embodiments, a DICOM header file is automatically written to, providing user preferences for display, and adding graphics to the image that can guide the user.

In various embodiments, a calibration target is provided that is sterilizable or disposable. Such targets include as size calibration object, calibration information, and color and greyscale reference target set such as. In some embodiments, a paper dot, rectangular object, or tape is printed with the image calibration pattern. In some embodiments, the shape of the object itself is the calibration size reference. In some embodiments, a microscopy slide or cover glass is printed with the calibration pattern. In some embodiments, a scalpel blade or handle, spreader, or other surgical device that would naturally fall within the field of view of the photo is printed with the calibration pattern. In some embodiments, the sterile drape surrounding a wound or surgical site is printed with the calibration pattern. In some embodiments, a wound dressing or bandage is printed with the calibration pattern.

In some embodiments, the calibration information is text (e.g., "1 inch" or "1 cm") along a ruler. However, in some embodiments, a bar code or a QR 2 dimensional code is included that eases automatic detection and can provide both dimensional and color reference information. Color reference patches may be either monochrome or color.

By including a barcode or QR code, the calibration target is self-describing in certain embodiments. For example, a QR code may be 1" in width and encode information about its own width along with information on reference swatches surrounding it (e.g., 100%, 95%, 50%, 5%, 0%).

In various embodiments, pixel shape correction parameters include scaling factors in one or two dimensions, for example to correct for parallax. In various embodiments, scale correction parameters include overall measurements of the field of view. In various embodiments, color correction parameters include adjustments to colorfulness, chroma, saturation, lightness, or brightness. In various embodiments, color correction parameters include red, green, blue (RGB) corrections or cyan, magenta, yellow, black (CMYK) correction. In various embodiments, contrast correction parameters include adjustments to contrast, brightness, window or level.

In various embodiments, images are processed automatically to detect the calibration object and then annotating the image header with the calibration information (e.g., in a DICOM image, the pixel spacing tag) or populate an external object such as a DICOM presentation state or registration object that references the original image to provide calibration information without having to modify the original image. The image calibration information then becomes available for use by downstream viewing systems and users.

In various embodiments, the lighting may be verified to be within predefined bounds (e.g., of color, brightness, or contrast) at image capture time. In such embodiments, a notification may be provided to the user or the image may be flagged if the color and exposure information is outside of the defined range. In this way, lighting or exposure can be corrected and the image re-captured promptly.

In various embodiments, a camera is provided that recognizes the calibration target object and then performs automatic white balance based on that object, irrespective of the overall attributed of the field of view.

In some embodiments, a microscopy slides or cover slides are provided. The calibration pattern may be imprinted such that it is nearly in focus with the typical slide preparation depths. In some embodiments, printing is provided as at one or more heights above the substrate.

Figure 3:
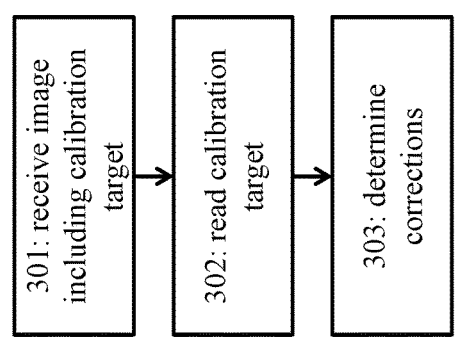
FIG. 3 illustrates a method of automated calibration of medical imagery according to embodiments of the present disclosure.

Referring now to FIG. 3, a method for automated calibration of medical imagery is illustrated according to embodiments of the present disclosure. At 301, a medical image is received. The medical image includes a calibration target in its field of view. At 302, a description of the calibration target is read from the calibration target. The description includes size and at least one color reference. At 303, based on the description of the calibration target, correction parameters are determined for the medical image. In some embodiments, the correction parameters include pixel shape correction parameters, scale correction parameters, contrast correction parameters, or color correction parameters.

Figure 4:
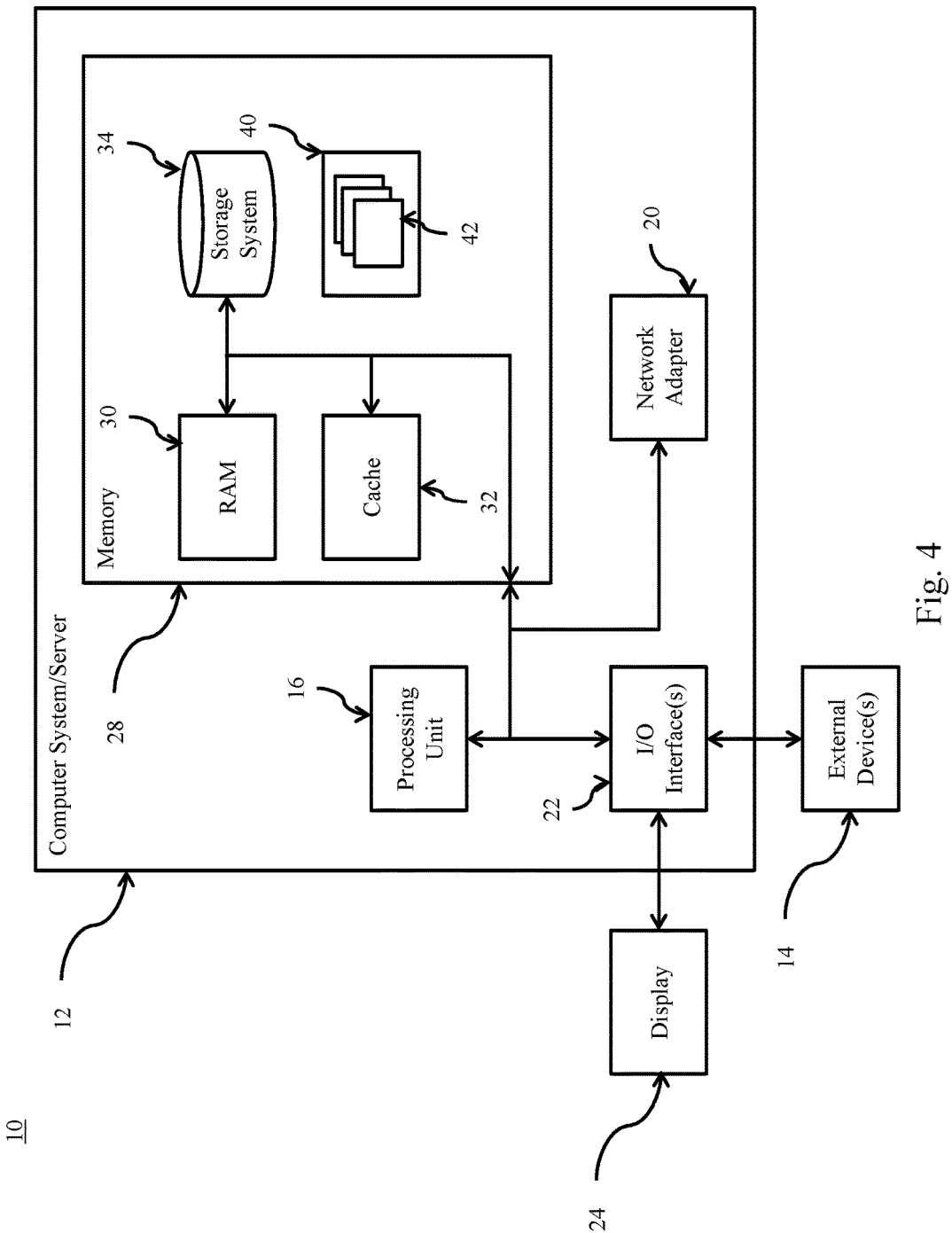
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
receiving a medical image including a calibration target, the calibration target having a size and at least one color, the calibration target comprising a self-descriptor and swatches of a plurality of different percentages of a single color, the self-descriptor comprising encoded information defining the size and the plurality of different percentages;
reading from the calibration target the self-descriptor of the calibration target;
based on the self-descriptor of the calibration target, determining correction parameters for the medical image, the correction parameters comprising pixel shape correction parameters, scale correction parameters, contrast correction parameters, or color correction parameters.

2. The method of claim 1, wherein the self-descriptor of the calibration target is encoded in a barcode.

3. The method of claim 1, wherein the self-descriptor of the calibration target is encoded in a QR code.

4. The method of claim 1, wherein the calibration target comprises a plurality of swatches.

5. The method of claim 1, wherein the calibration target is printed on paper, tape, a tool handle, a drape, or a dressing.

6. The method of claim 1, further comprising prompting a user to capture a corrected image.

7. The method of claim 1, further comprising annotating the medical image with the correction parameters.

8. The method of claim 7, wherein annotation the medical image comprises writing a DICOM header.

9. The method of claim 1, further comprising applying the correction parameters to correct the medical image.

10. The method of claim 1, further comprising applying pixel size, shape calibration, or window/level parameters to the medical image.

11. A computer program product for automated calibration of medical imagery, the computer program product comprising a computer readable storage medium having program instructions embodied therewith, the program instructions executable by a processor to cause the processor to perform a method comprising:

receiving a medical image including a calibration target, the calibration target having a size and at least one color, the calibration target comprising a self-descriptor and swatches of a plurality of different percentages of a single color, the self-descriptor comprising encoded information defining the size and the plurality of different percentages;

reading from the calibration target the self-descriptor of the calibration target;

based on the self-descriptor of the calibration target, determining correction parameters for the medical image, the correction parameters comprising pixel shape correction parameters, scale correction parameters, contrast correction parameters, or color correction parameters.

12. The computer program product of claim 11, wherein the self-descriptor of the calibration target is encoded in a barcode.

13. The computer program product of claim 11, wherein the self-descriptor of the calibration target is encoded in a QR code.

14. The computer program product of claim 11, wherein the calibration target comprises a plurality of swatches.

15. The computer program product of claim 11, wherein the calibration target is printed on paper, tape, a tool handle, a drape, or a dressing.

16. The computer program product of claim 11, further comprising prompting a user to capture a corrected image.

17. The computer program product of claim 11, further comprising annotating the medical image with the correction parameters.

18. The computer program product of claim 17, wherein annotation the medical image comprises writing a DICOM header.

19. The computer program product of claim 11, further comprising applying the correction parameters to correct the medical image.

20. The computer program product of claim 11, further comprising applying pixel size, shape calibration, or window/level parameters to the medical image.

\* \* \* \* \*